(12) United States Patent
Lee

(10) Patent No.: US 10,055,962 B2
(45) Date of Patent: *Aug. 21, 2018

(54) METHOD AND APPARATUS FOR PROVIDING AN EMERGENCY NOTIFICATION FOR AN ALLERGIC REACTION

(71) Applicant: AT&T Intellectual Property I, L.P., Atlanta, GA (US)

(72) Inventor: Brian Lee, Plainfield, IL (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/824,708

(22) Filed: Nov. 28, 2017

(65) Prior Publication Data

US 2018/0082561 A1 Mar. 22, 2018

Related U.S. Application Data

(63) Continuation of application No. 15/450,057, filed on Mar. 6, 2017, now Pat. No. 9,847,005, which is a continuation of application No. 14/475,237, filed on Sep. 2, 2014, now Pat. No. 9,589,443.

(51) Int. Cl.
| | |
|---|---|
| *G08B 1/08* | (2006.01) |
| *G08B 21/04* | (2006.01) |
| *A61B 5/00* | (2006.01) |
| *A61M 5/00* | (2006.01) |

(Continued)

(52) U.S. Cl.
CPC ............ *G08B 21/043* (2013.01); *A61B 5/411* (2013.01); *A61M 5/00* (2013.01); *G08B 25/016* (2013.01); *G08B 25/10* (2013.01); *A61M 2205/3584* (2013.01)

(58) Field of Classification Search
CPC .................................. A61M 1/00; A61B 1/00
See application file for complete search history.

(56) References Cited

U.S. PATENT DOCUMENTS

| | | |
|---|---|---|
| 6,517,517 B1 | 2/2003 | Farrugia et al. |
| 6,572,542 B1 | 6/2003 | Houben et al. |
| 7,261,691 B1 | 8/2007 | Asomani |

(Continued)

FOREIGN PATENT DOCUMENTS

| | | |
|---|---|---|
| CN | 201798970 U | 4/2011 |
| CN | 203107453 U | 8/2013 |

(Continued)

OTHER PUBLICATIONS

"New EpiPen® Adrenaline Auto-injector !Phone app from Alphapharm," Aug. 18, 2013. pp. 1.

(Continued)

*Primary Examiner* — Shirley Lu

(57) ABSTRACT

A method and an apparatus for providing a notification of a usage of a medical injector are disclosed. For example, the method determines location information of the medical injector. The method then detects the usage of the medical injector, and records a time of the usage of the medical injector. The method then sends the notification comprising the time at which the usage of the medical injector is detected and the location information of the medical injector.

18 Claims, 4 Drawing Sheets

(51) Int. Cl.
*G08B 25/10* (2006.01)
*G08B 25/01* (2006.01)

(56) References Cited

U.S. PATENT DOCUMENTS

| | | | |
|---|---|---|---|
| 7,390,319 B2 | 6/2008 | Friedman | |
| 7,988,630 B1 | 8/2011 | Osorio et al. | |
| 8,044,778 B2 | 10/2011 | Monroe | |
| 8,149,111 B2 | 4/2012 | Monroe | |
| 8,206,340 B2 | 6/2012 | Arefieg | |
| 8,313,463 B2 | 11/2012 | Barrow-williams et al. | |
| 8,639,288 B1 | 1/2014 | Friedman | |
| 2006/0069326 A1* | 3/2006 | Heath | A61H 31/005 601/41 |
| 2008/0020794 A1 | 1/2008 | Garon et al. | |
| 2009/0128330 A1* | 5/2009 | Monroe | A61M 5/002 340/568.1 |
| 2010/0227585 A1 | 9/2010 | Carroll et al. | |
| 2011/0093908 A1* | 4/2011 | Van Vleck | H04N 5/4403 725/106 |
| 2011/0230161 A1 | 9/2011 | Newman | |
| 2012/0046606 A1* | 2/2012 | Arefieg | A61B 5/0022 604/66 |
| 2013/0172689 A1 | 7/2013 | Dossas et al. | |
| 2013/0184649 A1 | 7/2013 | Edwards et al. | |
| 2014/0148120 A1 | 5/2014 | Buck | |

FOREIGN PATENT DOCUMENTS

| | | |
|---|---|---|
| DE | 69824884 T2 | 8/2005 |
| EP | 0616541 | 9/1994 |

OTHER PUBLICATIONS

"Auvi-Q™ (epinephrine injection, USP) : Watch and Learn". Nov. 2013. pp. 1-2.

"Dey Pharma Launches MyEpiPen Apps for IPhone and IPad: New Apps Feature an EpiPen® Auto-Injector Video Demonstration and Shareable Severe Allergy Profile,"investor.nnylan.conn, Jan. 20, 2011. pp. 1-2.

Kaiser, Reinhard, et al, "The application of geographic information systems and global positioning systems in humanitarian emergencies: lessons learned, programme implications and future research," Disasters 27.2 (2003): 127-140.

* cited by examiner

METHOD AND APPARATUS FOR PROVIDING AN EMERGENCY NOTIFICATION FOR AN ALLERGIC REACTION

This application is a continuation of U.S. patent application Ser. No. 15/450,057, filed Mar. 6, 2017, which is a continuation of U.S. patent application Ser. No. 14/475,237, filed Sep. 2, 2014, now U.S. Pat. No. 9,589,443, which are herein incorporated by reference in their entirety.

The present disclosure relates generally to providing an emergency notification for an allergic reaction, e.g., over a wireless network such as a long term evolution (LTE) based wireless network, and the like.

BACKGROUND

Severe allergic reaction affects millions of people around the world. Life-threatening allergic reactions may result from foods, e.g., peanuts, shellfish, various fruits, or insect bites or stings such as bee stings, or wasp stings, or any other environmental reactants in general. To address this potential life threatening event, vulnerable individuals may carry medication to be administered in case of emergency. For example, an individual may carry an epinephrine auto-injector, e.g., an EpiPen®, an Auvi-Q™, etc. to be administered when the individual is inadvertently exposed to an allergen. Applying the epinephrine auto-injector is only a temporary measure. Namely, administering of the epinephrine provides the affected individual with a small window of opportunity to receive further emergency medical attention in the critical minutes that follow. However, critical time may be wasted between the injection of the epinephrine and the follow up life-saving medical care. For example, if the allergic reaction occurred in an unfamiliar location, an affected individual calling for medical help may not be able to provide an accurate description of the location or address at which the emergency occurred. In another example, the affected individual may be in a panic or partially incapacitated after the exposure to the allergen and is unable to provide accurate location information.

SUMMARY OF THE DISCLOSURE

In one embodiment, the present disclosure describes a method and apparatus providing a notification of a usage of a medical injector, e.g., over a wireless network. For example, the method determines location information of the medical injector. The method then detects the usage of the medical injector, and records a time of the usage of the medical injector. The method then sends the notification comprising the time at which the usage of the medical injector is detected and the location information of the medical injector.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly describes a method and apparatus providing an emergency notification for an allergic reaction. Although the teachings of the present disclosure are discussed below in the context of a long term evolution (LTE) based wireless network, the teaching is not so limited. Namely, the teachings of the present disclosure can be applied via any other types of wireless networks (e.g., 2G network, 3G network, and the like), wherein providing an emergency assistance to an individual suffering from an allergic reaction may be beneficial.

In one embodiment, the method provides an epinephrine auto-injector that is able to determine and provide information as to its location (e.g., physical geographic location). Although, epinephrine auto-injectors are discussed in the present disclosure, the present disclosure is not so limited. Namely, the present disclosure is broadly applicable to a medical injector for delivering a medication to an affected individual who is suffering from an allergic reaction. Thus, the teachings of the present disclosure are not limited to a specific type of epinephrine auto-injector.

The medical injector of the present disclosure may utilize any location technology or system, e.g., global navigation satellite system (GNSS) such as Global Positioning System (GPS), Galileo or GLONASS, for determining its own physical location. For example, a GPS receiver of the medical injector may be used to determine the latitudinal and longitudinal coordinate at which the medical injector is located. In one embodiment, the medical injector may also indicate the altitude such that a location may be more precisely indicated in multistory buildings, underground transportation systems (e.g., train stations), etc.

In one embodiment, the medical injector may also have a Machine-to-Machine (M2M) communications capability for providing an emergency notification when the medical injector is used or triggered (i.e., when the medication is dispensed from the medical injector). In one embodiment, the medical injector may comprise a wireless fidelity (Wi-Fi), a cellular, or any other wireless communication interface. When triggered, the medical injector of the present disclosure is capable of sending a notification comprising a time of injection and the physical location information of the medical injector (broadly deemed to be the location of a "potential patient" who needs immediate medical attention) to any number of recipients. For example, the sending of the notification is automatically triggered upon detection of a usage of the medical injector, e.g., upon detecting that the EpiPen® or the Auvi-Q™ is used. The term "intended patient" or "potential patient" refers to a person for whom the medical injector is planned to be administered. For example, if a particular medical injector is to be injected into a person A, in case of an allergic reaction, then person A is the intended patient.

Figure 1:
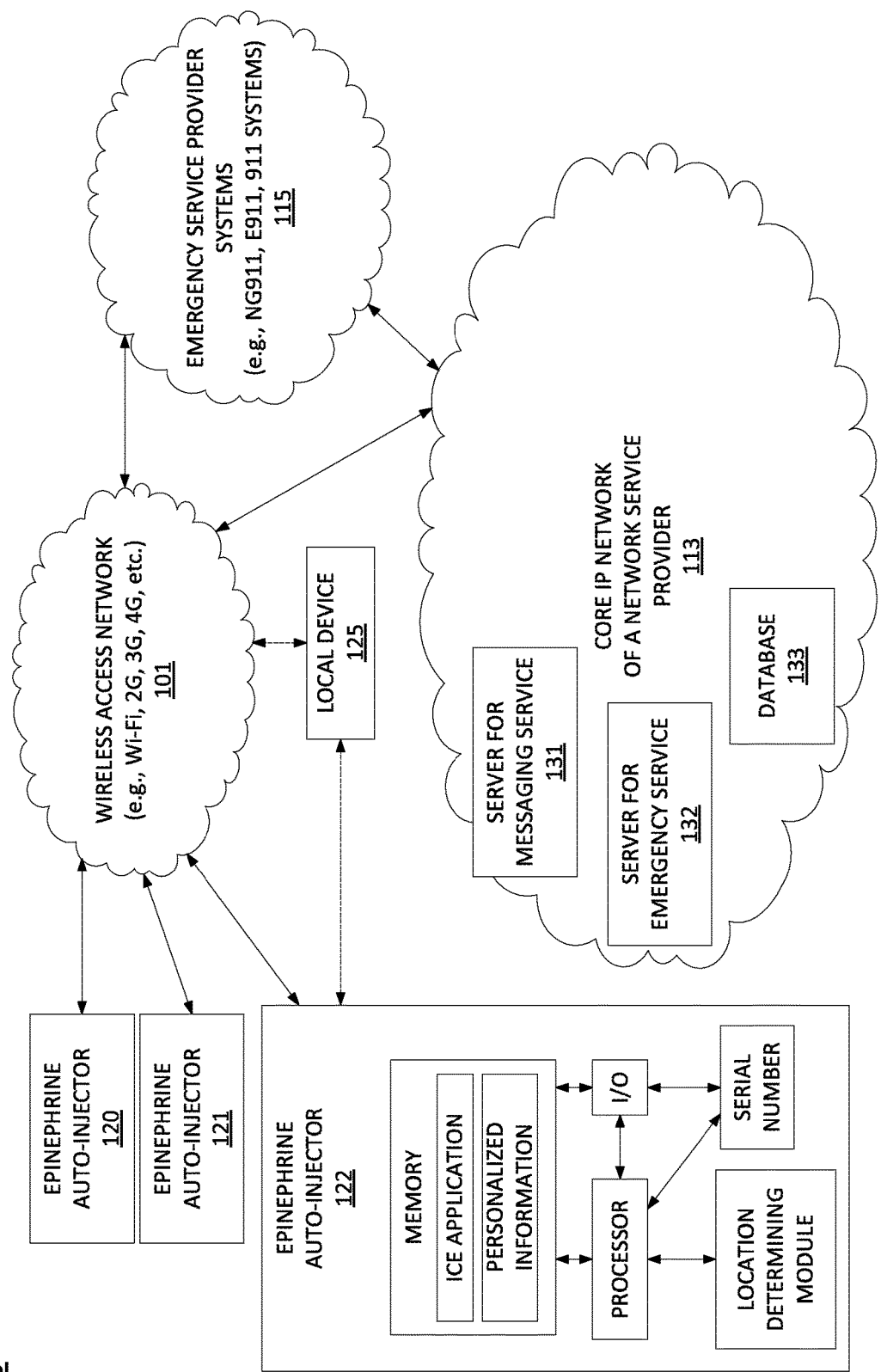
FIG. 1 illustrates an exemplary network related to the present disclosure.

FIG. 1 illustrates an exemplary network 100 related to the present disclosure. In one illustrative embodiment, the network 100 comprises a wireless network 101, a core network 113, and emergency service provider system 115. The wireless network 101 may comprise any number of wireless access networks, e.g. Wi-Fi networks, 2G networks, 3G networks, LTE networks, etc. The core network may comprise any number of application servers, gateway devices, routers, and switches of a network service provider. For example, the core network 113 may comprise a server 131 for providing a messaging service, an application server 132 for providing the emergency dispatch service of the present disclosure, and a database 133. The database 133 may be used for storing data, e.g., personalized information of intended patients, serial numbers of medical injectors, and a list of contacts for each intended patient for receiving the notification, e.g., emergency service providers, primary physicians, parents, guardians, roommates, family members, school officials of an educational institution, and the like. The emergency service provider system 115 may comprise any number and type of emergency service provider systems. For example, the emergency service provider system may comprise one or more of: an NG911 system, an E911 system, and a 911 system.

FIG. 1 also illustrates various epinephrine auto-injectors 120-122 (broadly medical injectors) and a local device 125. The epinephrine auto-injectors 120-122 are equipped with wireless capabilities as well as capabilities to determine their respective physical locations. Each epinephrine auto-injector is assigned a unique serial number that can be transmitted when the epinephrine auto-injector is triggered. In one embodiment, the local device comprises: a mobile phone such as a smart phone associated with the intended patient, a smart phone in the vicinity of the intended patient with a capability to relay notification messages, a server, a router, etc. For example, a Wi-Fi hotspot device, a mobile hotspot device, etc., may serve as a local device.

It should be noted that although various networks and network elements are shown separately in FIG. 1, it is possible that functions performed by these networks and network elements can be combined into fewer networks and/or network elements, or expanded into a greater number of networks and/or network elements depending on the deployment requirements.

It should also be noted that the above illustrated network 100 is only illustrative and the number of network components or elements are not specifically limited as shown. Any number of network components or elements can be deployed. For example, there may be several wireless networks, emergency service provider networks, core networks for several network service providers. In addition, any number of network elements may be deployed in each of the networks.

In one embodiment, a medical injector may send a notification to the emergency service provider system 115 via the wireless network 101. In another embodiment, the medical injector may send the notification to the emergency service provider system 115 via the wireless network 101 and the core network 113. In yet another embodiment, the medical injector may send the notification via the local device 125. In turn, the local device 125 relays the notification towards the emergency service provider system 115 via the wireless network 101 and/or the core network 113.

In one embodiment, the notification comprises personalized information of the intended patient. In one embodiment, the intended patient, a caregiver, a physician, a parent or any other authorized person, may configure the personalized information of the intended patient in the medical injector. The personalized information comprises any information that may be needed in case of emergency. For example, in one embodiment, the medical injector may comprise an In-Case-of-Emergency (ICE) Application (App). The intended patient or a caregiver may interact with the ICE App and enter emergency contacts (e.g., a family member, a guardian, a next of kin, a caregiver, a doctor, a neighbor, a school official, a nurse, etc. and their respective phone numbers, email addresses, etc.), relationship to intended patient for each emergency contact, a list of allergen triggers associated with the intended patient's allergic reaction (e.g., peanut, any number and types tree nuts, pollen, dairy, egg, wheat, soy, bee sting, wasp sting, etc.), the intended patient's statistics (e.g., age, gender, weight, etc), other medications taken by the intended patient, and any other health pertinent data (e.g., other illnesses or health conditions that may affect medical treatment).

In one embodiment, the medical injector may download the personalized information from another location, e.g., a server. For the example of FIG. 1, the personalized information may be stored in the database 133 located in network 113 and retrieved via the application server 132, as needed. In some scenarios, storing the personalized information in the network service provider's network has certain advantages. For instance, the intended patient, doctor, or caregiver may prefer having the personalized information located in a more secure environment. In case the intended patient misplaces the medical injector, the personalized information stored in the server of the service provider would not be compromised. In addition, if the medical injector is lost or destroyed, the personalized information would not need to be configured in a new medical injector. Rather, the new medical injector's serial number would be registered in the server and correlated with the intended patient, thereby reducing the amount of work needed by the intended patient and/or caregiver to keep the most up to date personalized information. In one embodiment, the personalized information may be accessed, updated and/or customized by the intended patient, caregiver, or a healthcare provider, via a mobile application and/or a web portal.

In one embodiment, in order to receive emergency notifications from medical injectors, the emergency service provider may subscribe to an emergency notification service from a network service provider. For example, if the network service provider stores the personalized information of a particular list of medical injector users, the subscription may enable the emergency service provider to seek permission to receive the personalized information. Upon being granted the permission, the emergency service provider may receive the emergency messages either directly from the medical injectors or through the network service provider.

In one embodiment, the notification comprises a serial number associated with the medical injector. For example, the serial number may be used to correlate a particular medical injector that has been used with a particular potential patient in need of emergency care. For example, the serial number of the medical injector may be provided to the server for storing with the personalized information of the potential patient. The serial number may be provided to the server either when the personalized information is configured or as an update. For example, a serial number of a new medical injector may be provided to the server as an update when the previous medical injector expires or is misplaced. It is important to note that any number of medical injectors may be registered for one particular individual. When the medical injector is applied, the medical injector may send its serial number to the server. The server may then use the serial number for correlating with a particular potential patient's personalized information. The server may then provide the personalized information to the emergency service provider automatically or as requested by the emergency service provider.

In one embodiment, the medical injector provides the notification directly to an emergency service provider, e.g., a 911, E911, NG911 service provider, serving the location at which the medical injector is physically located. In another embodiment, the notification may be sent to an application server of a network service provider. For example, a centralized application server of a network service provider may receive and process the messages from medical injectors as a subscribed service, and augment any additional information when available, and then notify the emergency service providers. In one example, the 911 service provider providing emergency services at the location at which the medical injector is located may not be capable of receiving notifications directly from medical injectors. In another example, the 911 service provider may not be able to receive a text message. Hence, the network service provider, e.g., AT&T® and the like, may receive the notification from the medical injector, convert the notification to a format appropriate for the emergency service provider, and then send the notification in the appropriate format to the 911 service provider. For instance, the network service provider may convert the text message described above to a voice format prior to forwarding to the 911 service provider.

As described above, the personalized information of the intended patient may be stored in a server of a network service provider or in the medical injector itself. If the personalized information is stored in the medical injector, the medical injector may directly provide the information to the emergency service provider directly, provided that the emergency service provider is capable of receiving the information directly from the medical injector. If the emergency service provider cannot receive the personalized information directly from the medical injector, the network service provider converts the information to the appropriate format prior to forwarding to the emergency service provider.

In one embodiment, if the personalized information is stored at the application server of the network service provider, the application server provides the personalized information to the medical injector, when the medical injector is used. For example, the usage of the medical injector may serve as a trigger for a communication to occur between the application server and the medical injector for the purpose of providing the information to the medical injector.

In one embodiment, the personalized information may also be sent to a display of the medial injection upon the injection being applied, e.g., in the event that the potential patient becomes incapacitated after the injection is applied. For example, a potential patient may become unconscious after the medical injector is applied. In such scenario, a care provider arriving at the scene may be able to see the personalized information displayed on the medical injector that has been used. It should be noted that the personalized information may optionally include additional updated medical information, e.g., recent medications or treatments received by the potential patient that may impact how the incapacitated patient should be treated.

In another embodiment, the medical injector sends a notification with its location information and serial number to the emergency service providers and to the application server. The application server may modify the notification by augmenting the notification with the personalized information of the intended patient. The network service provider may then further notify the emergency service provider, with the modified notification. The emergency service provider may then receive the time of injection, the location information, and the serial number, without waiting for the duration of time needed for identifying the intended patient and retrieving the personalized information of the intended patient. The emergency service provider may then dispatch emergency personnel as soon as possible. In turn, the modified notification may then be received by the emergency personnel for use during treatment of the patient.

In one embodiment, the network service provider may perform additional notifications to other recipients. For example, there may be a previously provided list of recipients. In one embodiment, the other recipients may comprise one or more of: a family member, a guardian, a next of kin, a caregiver, a doctor, a neighbor, a school official, a nurse, and the like.

In one embodiment, the medical injector is able to communicate with other local devices, e.g., smart phones, Wi-Fi servers, etc. When the medical injector is triggered, the medical injector may then send its location information its serial number, and/or personalized information of the intended patient via the other local devices. The other local devices may then relay the information to the 911 service provider, e.g., an NG911 system serving the location at which the medical injector is physically located and/or the network service provider. If the information is relayed to the network service provider, the network service provider forwards the information to the emergency service provider. If the personalized information of the intended patient is not included in the information received by the network service provider, the network service provider may augment the necessary information, as needed. Similar to the scenario described above, the network service provider may also perform additional notifications to other recipients.

In one embodiment, the local device may not be a personal device associated with the patient. For example, the local device may be a publicly usable Wi-Fi server. In another embodiment, the local device may be a personal device associated with the potential patient. For example, the local device may be the potential patient's smart phone. In which case, the local device may also be configured to provide additional information that the patient may not have stored in the medical injector. For example, the smart phone may be able to access the potential patient's medical information from another location, e.g., a doctor's record, an insurance company record, a hospital record, or a pharmacy record, that may be stored at other locations, i.e., remote from the potential patient's current location. The smart phone of the potential patient may then send the additional information to the emergency service provider and/or the network service provider. The additional information is sent along with the notification.

Figure 2:
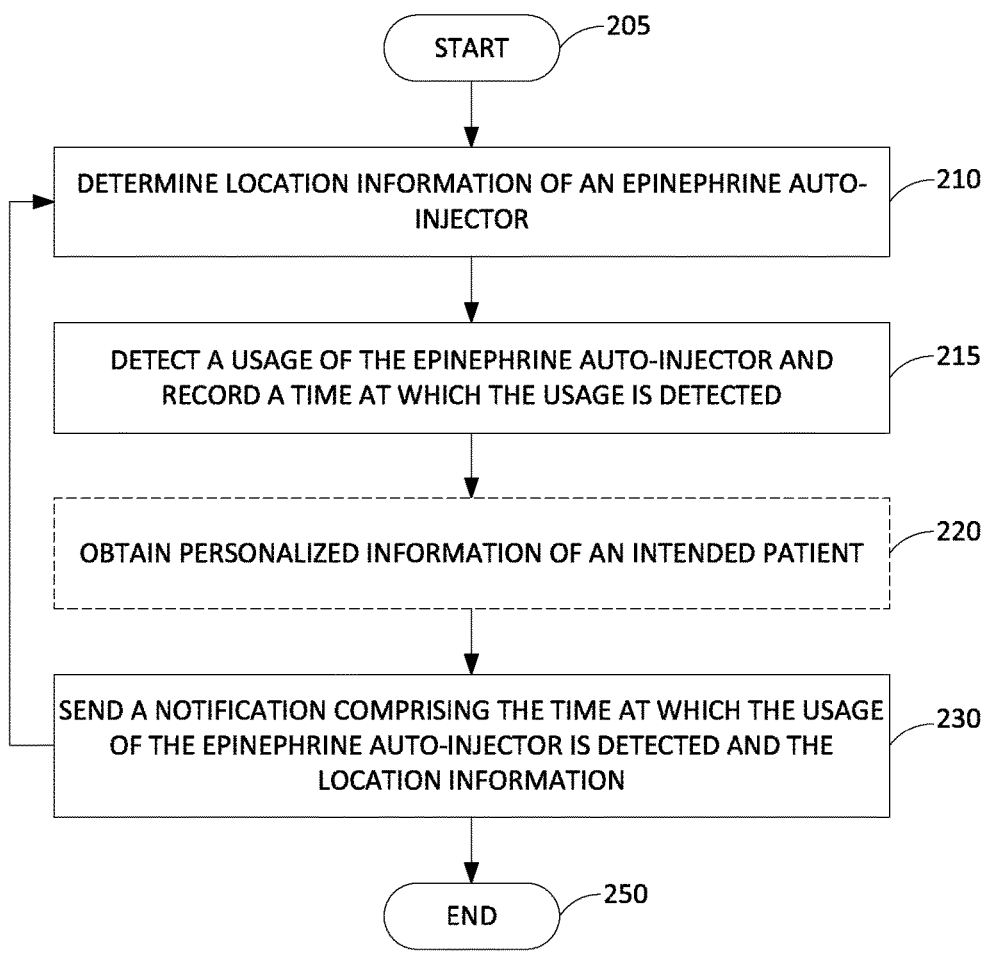
FIG. 2 illustrates a method of the present disclosure for providing an emergency notification for an allergic reaction implemented in an epinephrine auto-injector.

FIG. 2 illustrates a method 200 of the present disclosure for providing an emergency notification for an allergic reaction implemented in an epinephrine auto-injector (broadly a medical injector). For example, the method may be implemented in an EpiPen® or an Auvi-Q™. Method 200 starts in step 205 and proceeds to step 210.

In step 210, method 200 determines location information of the epinephrine auto-injector. For example, (e.g., physical location) information of the epinephrine auto-injector may be determined by utilizing a Global Positioning System (GPS) receiver of the epinephrine auto-injector. In one embodiment, the location information comprises the latitudinal and longitudinal coordinate at which the epinephrine auto-injector is located. In one embodiment, the epinephrine auto-injector may also indicate the altitude at which the epinephrine auto-injector is located.

In step 215, method 200 detects a usage of the epinephrine auto-injector and records a time at which the usage is detected. For example, the usage of the medical injector triggers a communication such that the emergency service provider is able to dispatch emergency personnel to the location at which the medical injector is administered to the potential patient.

In optional step 220, method 200 obtains personalized information of an intended patient. The personalized information comprises information that may be used, in case of emergency, to provide emergency care to the intended patient after the usage of the epinephrine auto-injector.

In one embodiment, the potential patient, a caregiver, a physician, or any other authorized person, may configure the personalized information of the intended patient in the medical injector. For example, in one embodiment, the medical injector may comprise an In-Case-of-Emergency (ICE) Application (App). The potential patient, or a caregiver may interact with the ICE App and enter the personalized information.

In one embodiment, the personalized information comprises one or more of: a list of emergency contacts and a means of reaching the emergency contacts (e.g., a family member, a guardian, a next of kin, a caregiver, a doctor, a neighbor, a school official, a nurse, etc. and their respective phone numbers, email addresses, etc.), relationship to the potential patient for each emergency contact, a list of triggers for the potential patient's allergic reaction (e.g., peanut, any number and types tree nuts, pollen, dairy, egg, wheat, soy, etc.), the potential patient's statistics (e.g., age, gender, weight, etc), other medications prescribed to the potential patient, and any other health pertinent data (e.g., other illnesses or health conditions that may affect treatment).

In one embodiment, the medical injector may obtain the personalized information from a server or a database of a network service provider. In one embodiment, the personalized information is obtained by the medical injector upon usage of the medical injector. For example, the usage of the medical injector may serve as a trigger for a communication to occur between the server and the medical injector for the purpose of providing the personalized information to the medical injector.

In one embodiment, the medical injector may obtain the personalized information via a local device. In one embodiment, the local device may be a personal device associated with the potential patient. For example, the local device may be the potential patient's smart phone. For example, the smart phone may be able to access the potential patient's personalized information, e.g., medical information from another location. The smart phone of the potential patient may then provide the personalized information to the medical injector.

In one embodiment, the personalized information may be accessed, updated and/or customized by a potential patient, caregiver, healthcare provider, etc. via a mobile application and/or a web portal.

In one embodiment, the personalized information is information to be accessed by an emergency service provider on a subscription basis. For example, if the network service provider stores the personalized information of a particular list of medical injector users, the subscription may enable the emergency service provider to seek permission to receive the personalized information of the particular list of medical injector users. Upon being granted the permission, the emergency service provider may receive the emergency notifications either directly from the medical injectors, or through the network service provider.

In step 230, method 200 sends a notification comprising the time at which the usage of the medical injector is detected and the location information. The method then proceeds to step 210 to continue determining a current location of the medical injector or to step 250 to end processing the present notification.

Figure 3:
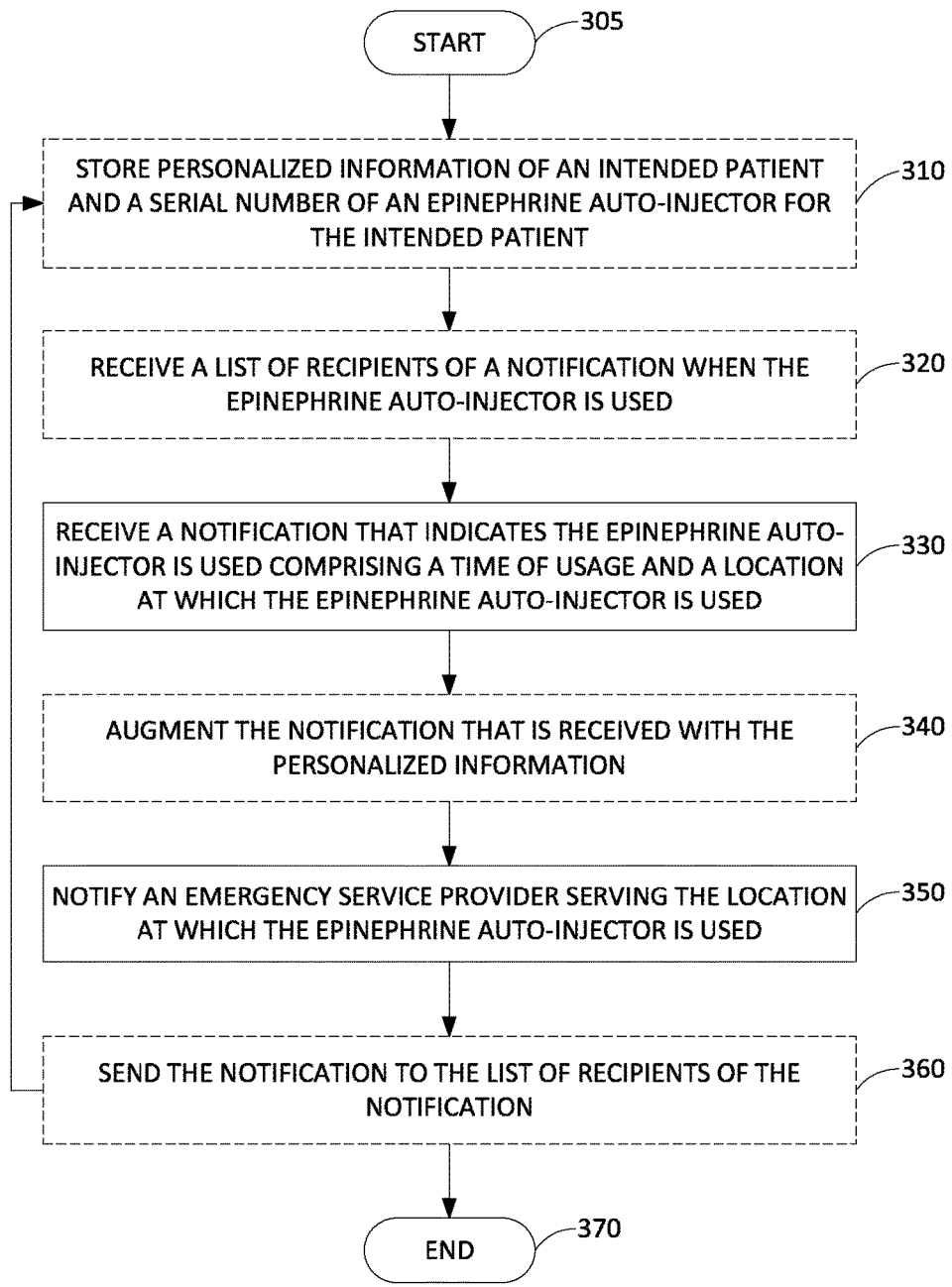
FIG. 3 illustrates a method of the present disclosure for providing an emergency notification for an allergic reaction implemented in a server of a service provider network.
Figure 4:
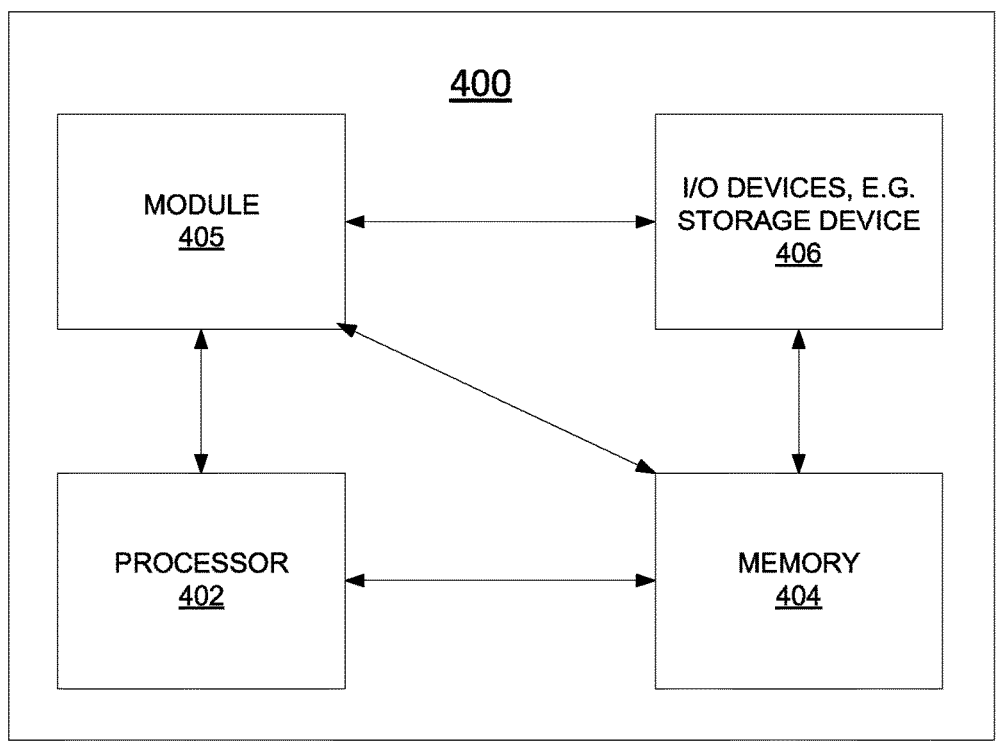
FIG. 4 depicts a high-level block diagram of a general-purpose computer suitable for use in performing the functions described herein.

FIG. 3 illustrates a method 300 of the present disclosure for providing an emergency notification for an allergic reaction implemented in a server or a general purpose computer as shown in FIG. 4 of a service provider network. Method 300 starts in step 305 and proceeds to step 310.

In optional step 310, method 300 stores personalized information of an intended patient and a serial number of an epinephrine auto-injector (broadly a medical injector) for the intended patient. For example, a user of an epinephrine auto-injector may register a particular epinephrine auto-injector's serial number and his/her personalized information. In one embodiment, the personalized information comprises one or more of: a list of emergency contacts and a means of reaching the emergency contacts (e.g., a family member, a guardian, a next of kin, a caregiver, a doctor, a neighbor, a school official, a nurse, etc. and their respective phone numbers, email addresses, etc.), relationship to the intended patient for each emergency contact, a list of triggers for the intended patient's allergic reaction (e.g., peanut, any number and types tree nuts, pollen, dairy, egg, wheat, soy, etc.), the intended patient's statistics (age, gender, weight, etc), other prescribed medications of the intended patient, and any other health pertinent data (e.g., other illnesses or health conditions that may affect treatment).

In optional step 320, method 300 receives a list of recipients of a notification when the medical injector is used. For example, a list of emergency contacts and a means of reaching the emergency contacts (e.g., a family member, a next of kin, a doctor, a neighbor, a school official, a nurse, etc. and their respective phone numbers, email addresses, etc.), and the like, may be received on a per use basis, i.e., when the medical injector is applied.

In step 330, method 300 receives a notification that indicates the medical injector is used. The notification comprises a time of usage, and a location at which the medical injector is used. In one embodiment, the notification further comprises the serial number of the medical injector. As described above, in one embodiment, the patient, caregiver, physician, or any other authorized person, may configure the personalized information of the intended patient in the medical injector. If the personalized information of the intended patient is stored in the medical injector, the notification further comprises the personalized information of the intended patient.

In optional step 340, method 300 augments the notification that is received with the personalized information. For example, if the personalized information is stored in the service provider's network, the server adds the personalized information to the notification that is received from the medical injector, thereby amending the notification that is received by adding the personalized information.

In step 350, method 300 notifies wirelessly an emergency service provider serving the location at which the medical injector is used, e.g., the physical location of the medical injector. The location information received from the medical injector indicates the location at which the medical injector is physically located. In one embodiment, the method notifies the emergency service provider prior to executing step 340, such that the notification occurs without delay. In one embodiment, the method 300 may optionally cause a phone call to be placed to the intended patient or a designated phone number to inquire about the deployment of the medical injector. This optional step allows for verification to be made before emergency services are summoned on behalf of the intended patient. The method may then perform step 340 and provide a further notification for use during treatment of the intended patient. In other words, steps 340 and 350 may occur in any order serially or in parallel.

In one embodiment, the emergency service provider providing emergency services at the location at which the medical injector is located may not be capable of receiving notifications directly from medical injectors or in a format the notification is received from the medical Injectors. For instance, the emergency service provider may not be able to receive a text message. Hence, method 300 may first convert the notification to a format appropriate for the emergency service provider prior to notifying the emergency service provider. For example, if the emergency service provider is not able to receive text messages, the method 300 may convert notifications that are in a text format to a voice format, prior to forwarding to the emergency service provider.

In optional step 360, method 300 sends the notification to the list of recipients of the notification. For example, the method sends the notification to the list of recipients received in step 320 or to the list of recipients previously registered in step 310, e.g., by the intended patient or a caregiver. The method either proceeds to step 370 to end processing the current notification or to step 310.

As such, the present disclosure provides at least one advancement in the technical field of medical injectors that provide a notification of the medical injector's use and its current location. This advancement is in addition to the traditional use of the medical injector as a vehicle for the delivery of a medication to an intended patient. Viewed in another manner, the present disclosure provides a transformation of the activation of a medical injector into a trigger for sending a notification of the medical injector's application and the medical injector's current location. Such notification can bring about a rapid response in summoning emergency services to a location in which the medical injector was triggered.

FIG. 4 depicts a high-level block diagram of a general-purpose computer suitable for use in performing the functions described herein. As depicted in FIG. 4, the system 400 comprises one or more hardware processor elements 402 (e.g., a central processing unit (CPU), a microprocessor, or a multi-core processor), a memory 404, e.g., random access memory (RAM) and/or read only memory (ROM), a module 405 for providing an emergency notification for an allergic reaction, and various input/output devices 406 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method 200 or 300 as discussed above is implemented in a distributed or parallel manner for a particular illustrative example, i.e., the steps of the above methods 200 and 300, or the entire method 200 or 300 are implemented across multiple or parallel general-purpose computers, then the general-purpose computer of this figure is intended to represent each of those multiple general-purpose computers.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 405 for providing an emergency notification for an allergic reaction (e.g., a software program comprising computer-executable instructions) can be loaded into memory 404 and executed by hardware processor element 402 to implement the steps, functions or operations as discussed above in connection with the exemplary method 200 or method 300. Furthermore, when a hardware processor executes instructions to perform "operations", this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for providing an emergency notification for an allergic reaction (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A method for providing a notification of a usage of a medical injector, the method comprising:
   determining, via a processor of a network service provider, location information of the medical injector;
   detecting, via the processor, the usage of the medical injector;
   recording, via the processor, a time of the usage of the medical injector; and
   sending, via the processor, the notification comprising the time at which the usage of the medical injector is detected and the location information of the medical injector, wherein the processor augments the notification with personalized information of an intended patient.

2. The method of claim 1, wherein the notification is sent to an emergency service provider.

3. The method of claim 2, wherein the notification is sent to the emergency service provider in a format that the emergency service provider is capable of processing the notification.

4. The method of claim 1, further comprising:
providing an additional notification to a list of recipients, wherein the list of recipients comprises one or more of: a family member, a guardian, a next of kin, a caregiver, a doctor, a neighbor, a school official, and a nurse.

5. The method of claim 1, wherein the location information comprises a latitudinal coordinate and a longitudinal coordinate at which the medical injector is located.

6. The method of claim 5, wherein the location information further comprises an altitude at which the medical injector is located.

7. A non-transitory computer-readable storage device storing a plurality of instructions which, when executed by a processor of a network service provider, cause the processor to perform operations for providing a notification of a usage of a medical injector, the operations comprising:
determining location information of the medical injector;
detecting the usage of the medical injector;
recording a time of the usage of the medical injector; and
sending the notification comprising the time at which the usage of the medical injector is detected and the location information of the medical injector, wherein the processor augments the notification with personalized information of an intended patient.

8. The non-transitory computer-readable storage device of claim 7, wherein the notification is sent to an emergency service provider.

9. The non-transitory computer-readable storage device of claim 8, wherein the notification is sent to the emergency service provider in a format that the emergency service provider is capable of processing the notification.

10. The non-transitory computer-readable storage device of claim 7, wherein the operations further comprise:
providing an additional notification to a list of recipients, wherein the list of recipients comprises one or more of: a family member, a guardian, a next of kin, a caregiver, a doctor, a neighbor, a school official, and a nurse.

11. The non-transitory computer-readable storage device of claim 7, wherein the location information comprises a latitudinal coordinate and a longitudinal coordinate at which the medical injector is located.

12. The non-transitory computer-readable storage device of claim 11, wherein the location information further comprises an altitude at which the medical injector is located.

13. An apparatus for providing a notification of a usage of a medical injector, the apparatus comprising:
a processor of a network service provider; and
a computer-readable storage device storing a plurality of instructions which, when executed by the processor, cause the processor to perform operations, the operations comprising:
determining location information of the medical injector;
detecting the usage of the medical injector;
recording a time of the usage of the medical injector; and
sending the notification comprising the time at which the usage of the medical injector is detected and the location information of the medical injector, wherein the processor augments the notification with personalized information of an intended patient.

14. The apparatus of claim 13, wherein the notification is sent to an emergency service provider.

15. The apparatus of claim 14, wherein the notification is sent to the emergency service provider in a format that the emergency service provider is capable of processing the notification.

16. The apparatus of claim 13, wherein the operations further comprise:
providing an additional notification to a list of recipients, wherein the list of recipients comprises one or more of: a family member, a guardian, a next of kin, a caregiver, a doctor, a neighbor, a school official, and a nurse.

17. The apparatus of claim 13, wherein the location information comprises a latitudinal coordinate and a longitudinal coordinate at which the medical injector is located.

18. The apparatus of claim 17, wherein the location information further comprises an altitude at which the medical injector is located.

* * * * *